US012694559B2

(12) United States Patent
Teixeira et al.

(10) Patent No.: US 12,694,559 B2
(45) Date of Patent: Jul. 28, 2026

(54) METHOD AND SYSTEMS FOR AUTOMATIC GANTRY TILT ESTIMATION FOR HEAD CT SCANS FROM CAMERA IMAGES

(71) Applicant: Siemens Healthineers AG, Forchheim (DE)

(72) Inventors: Brian Teixeira, Princeton, NJ (US);
Vivek Singh, Princeton, NJ (US);
Ankur Kapoor, Plainsboro, NJ (US);
Andreas Prokein, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 525 days.

(21) Appl. No.: 18/166,508

(22) Filed: Feb. 9, 2023

(65) Prior Publication Data

US 2024/0273754 A1     Aug. 15, 2024

(51) Int. Cl.
*G06T 7/73*         (2017.01)
*A61B 6/00*         (2024.01)

(52) U.S. Cl.
CPC .............. *G06T 7/73* (2017.01); *A61B 6/4435* (2013.01); *A61B 6/4447* (2013.01); *G06T 2207/10024* (2013.01); *G06T 2207/30004* (2013.01); *G06T 2207/30201* (2013.01)

(58) Field of Classification Search
CPC .............. G06T 7/73; G06T 2207/10024; G06T 2207/30004; G06T 2207/30201; A61B 6/107; A61B 6/469; A61B 6/545; A61B 6/547; A61B 6/032; A61B 6/035; A61B 6/501; A61B 6/58; A61B 6/589
See application file for complete search history.

(56) References Cited

U.S. PATENT DOCUMENTS

| | | | |
|---|---|---|---|
| 2015/0104092 A1 | 4/2015 | Flohr et al. | |
| 2018/0247427 A1 | 8/2018 | Geiger et al. | |
| 2019/0057515 A1* | 2/2019 | Teixeira ................. | A61B 6/488 |
| 2019/0231296 A1* | 8/2019 | Jackson ................. | A61B 6/488 |
| 2020/0104695 A1* | 4/2020 | Laaksonen ............. | G16H 50/70 |
| 2022/0022836 A1* | 1/2022 | Contijoch .............. | A61B 6/542 |

FOREIGN PATENT DOCUMENTS

WO     WO-2022232749 A1 * 11/2022    ........... A61B 5/7267

OTHER PUBLICATIONS

EP search report in EP application No. 24156590.2, dated Jul. 26, 2024, 8 pages.
Filice, Ross. "Lens identification to prevent radiation-induced cataracts using convolutional neural networks." Journal of Digital Imaging 32.4 (2019): 644-650.

* cited by examiner

*Primary Examiner* — Shefali D Goradia

(57)         ABSTRACT
Systems and methods for estimating optimal gantry orientation and/or scanning parameters using image(s) from one or several cameras for a CT scan of a patient. Images are acquired of a patient. An optimal gantry tilt is estimated that keeps the patient's eye lenses outside a range of a beam during the scan. The CT scan is performed using the optimal gantry tilt. A scout scan is not used.

18 Claims, 8 Drawing Sheets

System 200

CAMERA 106

CONTROL UNIT 201

MEMORY 103

PROCESSOR 102

DISPLAY 104

GANTRY TILT CONTROL 112

PATIENT 110

TABLE 120

BORE 130

GANTRY 108

Orientation Box 701

METHOD AND SYSTEMS FOR AUTOMATIC GANTRY TILT ESTIMATION FOR HEAD CT SCANS FROM CAMERA IMAGES

FIELD

The present embodiments relate to positioning during a medical imaging scan.

BACKGROUND

During a CT scan, a patient is positioned on a surface/bed that slowly moves through a gantry while an x-ray tube rotates around the patient, shooting narrow beams of x-rays through the body. CT scanners use special digital x-ray detectors that are located directly opposite the x-ray source. As the x-rays leave the patient, they are picked up by the detectors and transmitted to a computer that processes the data into an image. The use of CT scans for patients with head injuries and convulsions has many benefits for medical diagnosis and analysis but has raised concerns due to the use of radiation during the procedure. CT scans use x-rays and all x-rays produce ionizing radiation. Ionizing radiation has the potential to cause biological effects in living tissue. This is a risk that increases with the number of exposures added up over the life of an individual.

Eye lenses are among the most sensitive organs to x-ray radiation and may be considered at risk during radiology procedures such as CT scans. The current available strategies to reduce the radiation dose to the eye lens region are limited. Current workflows for head scans attempt to keep the eye lenses outside the range of the beam in two different ways. A technician may either manually position and orient the patient's head, or (when available) use a gantry tilt function of the scanner. Currently, tilting is estimated based on a region of interest estimated on a previous scout scan. Both approaches have drawbacks. The first approach requires manual input for the technician and is highly subject to errors since the technician can only give an estimate of the internal anatomy. The second approach, while being more precise require a scout scan which is time consuming and may still cause errors if the patient moves their head after the scout scan. These issues become increasingly concerning when dealing with trauma cases where time and accuracy are crucial.

SUMMARY

In a first aspect, a system is provided for estimating an optimal gantry orientation for a CT scan without using a scout scan. The method includes acquiring, by at least one camera, one or more images of a patient; estimating, using a machine learning system, 3D internal landmarks of the patient from the one or more images; defining one or more protocol dependent 3D orientation boxes based on the 3D internal landmarks; determining the optimal gantry orientation based on the one or more protocol dependent 3D orientation boxes; and performing the CT scan, by a CT scanner, wherein a gantry of the CT scanner is positioned using the optimal gantry orientation.

In a second aspect, a method is provided for estimating gantry orientation of a gantry for a CT scan without using a scout scan. The method includes acquiring, by at least one camera, one or more images of a patient; determining, using a machine learning system, an optimal gantry orientation from the one or more images; and performing the CT scan, wherein the gantry is positioned using the optimal gantry orientation.

In a third aspect a system is provided for estimating gantry orientation for CT scans without using a topogram. The system includes at least one camera, a CT scanning system, and a control unit. The at least one camera is configured to acquire one or more images of a patient. The CT scanning system is configured to perform a scan of the patient, the CT scanning system comprising at least a gantry and a gantry control system. The control unit is configured to determine an optimal gantry orientation based on the one or more images and adjust the CT gantry using the gantry control system.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

Embodiments provide systems and methods for estimating optimal gantry tilt and/or scanning parameters using image(s) from one or several cameras for a CT scan of a patient. As the patient enters the gantry, embodiments use the image(s) to estimate internal landmarks of anatomical head and neck structures of the patient including but not limited to eyes, sinuses, inner ear, jaw, and the patient's skull. With the location of these internal structures known, protocol-dependent orientation boxes may be defined and used to define a scan range and a gantry orientation.

Figure 1:
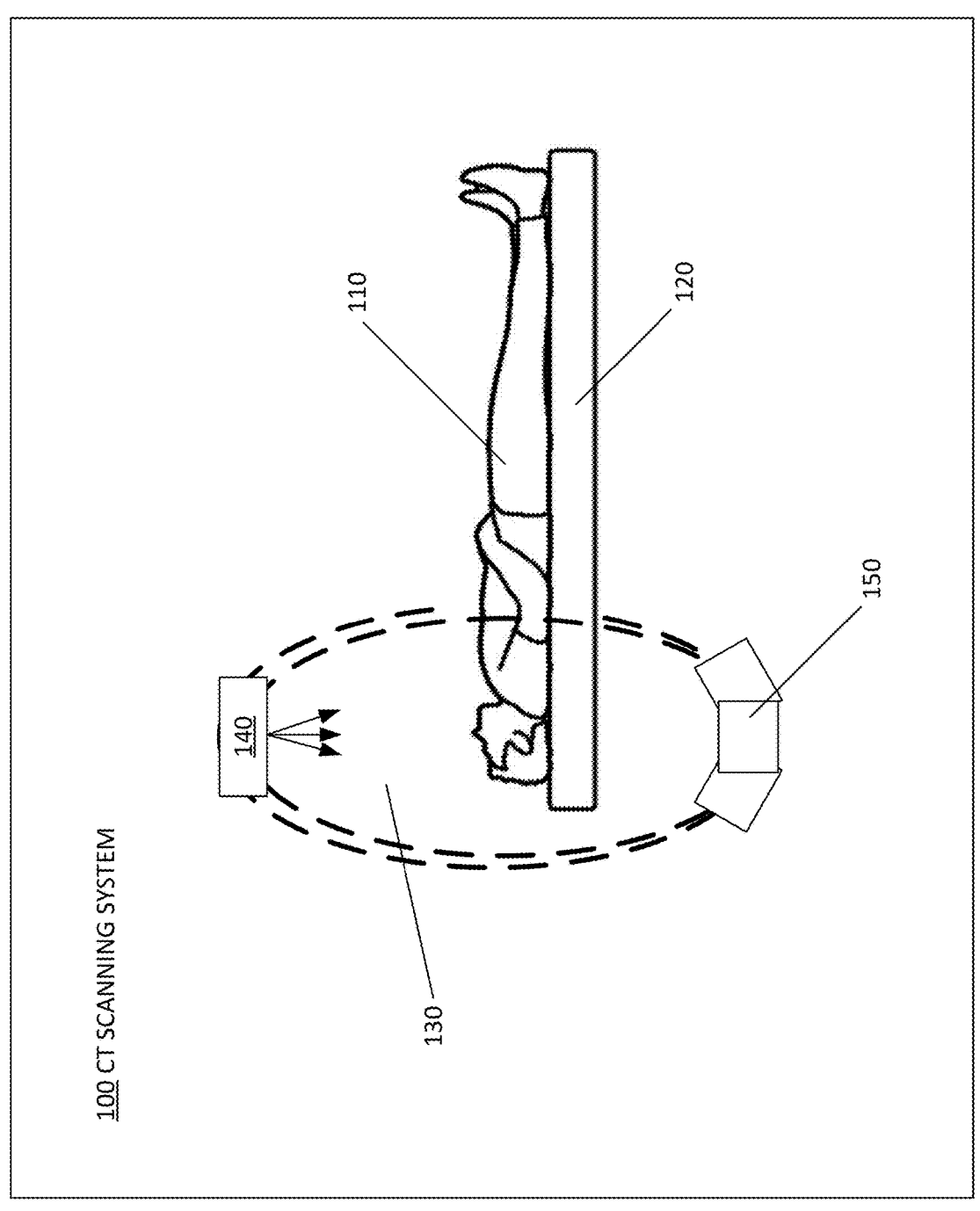
FIG. 1 depicts an example CT scanning system.

FIG. 1 depicts an example CT imaging system 100. An object 110 (e.g., a patient 110) is positioned on a table 120 that is configured, via a motorized system, to move the table 120 to multiple positions through a circular opening 130 in the CT imaging system 100. An X-ray source 140 (or other radiation source) and detector element(s) 150 are a part of the CT imaging system 100 and are configured to rotate around the subject 110 on a gantry while the subject is inside the opening/bore 130. The rotation may be combined with movement of the bed to scan along a longitudinal extent of the patient 110. Alternatively, the gantry moves the source 140 and detector 150 in a helical path about the patient 110. In a CT imaging system 100, a single rotation may take approximately one second or less. During the rotation of the X-ray source 140 and/or detector, the X-ray source 140 produces a narrow, fan-shaped (or cone-shaped) beam of X-rays that pass through a targeted section of the body of the subject 110 being imaged. The detector element(s) 150 (e.g., multi-ring detector elements) are opposite the X-ray source 140 and register the X-rays that pass through the body of the subject being imaged and, in that process, record a snapshot used to create an image. Many different snapshots at many angles through the subject are collected through one or more rotations of the X-ray source 140 and/or detector element(s) 150. The image data generated by the collected snapshots are transmitted to a control unit that stores or processes the image data based on the snapshots into one or several cross-sectional images or volumes of an interior of the body (e.g., internal organs or tissues) of the subject being scanned by the CT imaging system 100.

While a CT scan is useful for certain medical diagnosis, the use of radiation is a drawback. When performing a head CT scan, one important detail is to keep the eye lenses outside the range of the beam as the eye lenses are very sensitive to radiation. During a typical CT of the brain, the eye receives approximately 50 milliGray (mGy), or 5 rads, of radiation depending on the protocol and type of machine. The lens of the eye is particularly radiosensitive; as little as 0.5-2 Gray (50-200 rads) causes detectable opacities, and exposures of over 4 Gray (400 rads) causes visual impairment secondary to cataracts. Controlling radiation exposure to the eye is important, especially in patients with visual impairment, cataracts, young or sensitive eyes, and in patients who require multiple scans. Radiation exposure may be reduced by otherwise excluding lens from the scanning area or region by optimizing the gantry tilt and scan length. The most efficient method for reducing lens dose is gantry tilting, for example by aligning the scan plane along the skull base to the radix nasi which leaves the lenses outside the primary radiation beam. However, tilting angles may vary due to patient-specific attributes and physiologic limitations. For each scan, a technician must set the gantry tilt so that the patient 110 is protected and a high-quality accurate scan may be achieved. One tool used for determining the level of gantry tilt is by using a preliminary or scout scan (topogram).

A preliminary or scout image is normally taken of a body region before a definitive imaging study—e.g., a scout scan before a CT scan. The scout scan serves to establish a baseline and may be used before performing any type of imaging procedure. There may be one or more reasons to get a scout scan: to make sure the region of interest is included in the field of view, to check the exposure technique, or as a baseline prior to administration of contrast material. In the case of a typical CT study, the scout scan is used to plot the locations where the subsequent slice images will be obtained. The scout scan may also be used as input for dose modulation software or other scanning parameters.

Embodiments provide a workflow that obviates the need for a scout scan and thus results in a significant boost in efficiency. Embodiments estimate the position of internal structures in the head and neck regions using image data from one or more cameras located in or around the CT system. The estimated internal structures are used to guide the position of the patient 110 in the gantry as well as estimate the tilt to be applied to the gantry to better constrain the scan to the region of interest. Embodiments provide a method for gantry tilt, scan range, and/or patient orientation estimation from RGBD images, without the need of a scout scan, in the context of head CT scans. Since embodiments work directly on camera images, they do not require a scout scan (topogram). By skipping the topogram, the radiation dose that is applied to the patient 110 is decreased. In addition, the overall time is greatly decreased for scanning a patient 110 which can be crucial in trauma cases. Moreover, since the method continuously estimates the position of internal structures in the head and neck, the method is more robust to patient movements. Overall, the method is faster, safer for the patient 110 and more cost effective.

Figure 2:
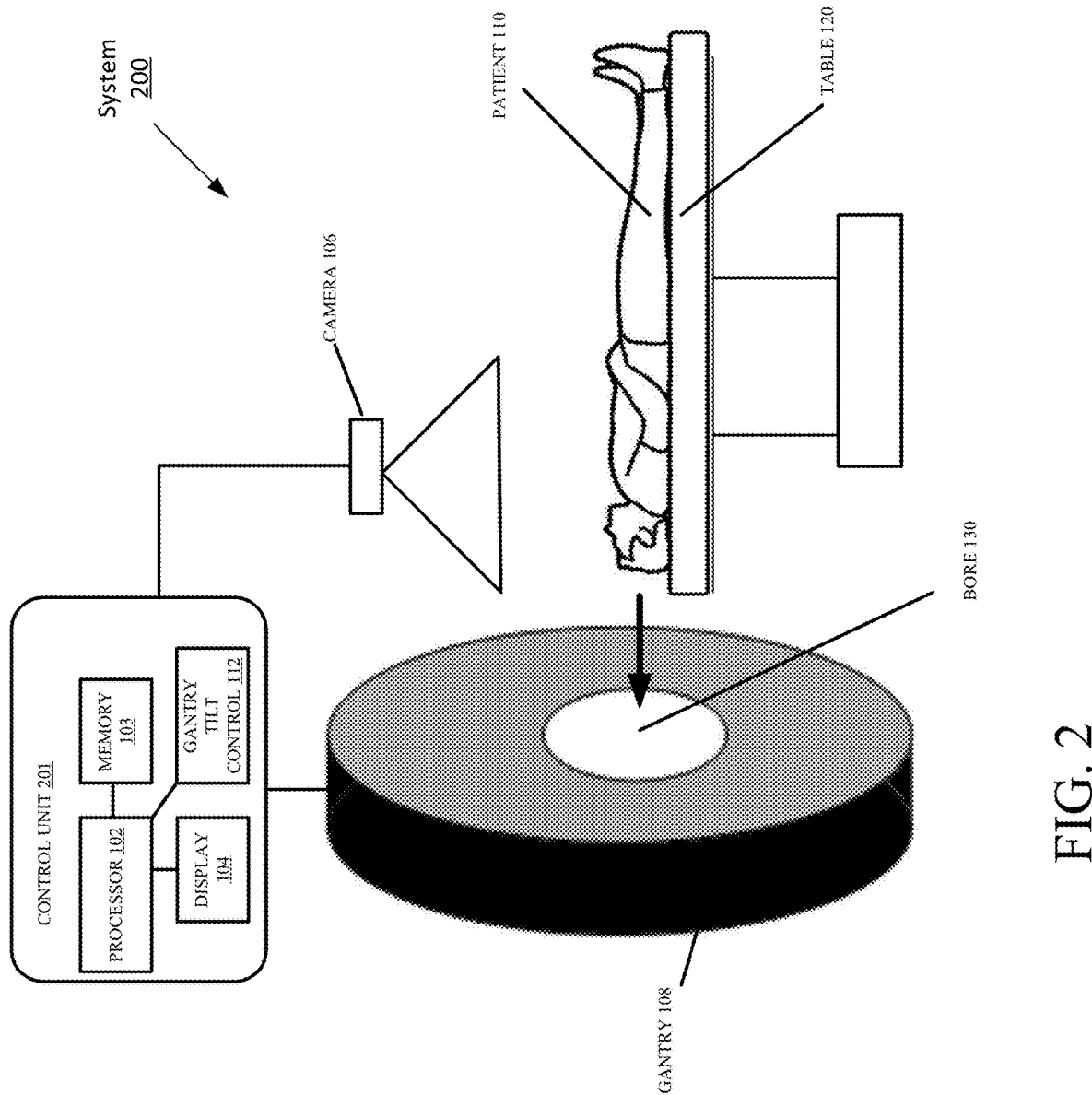
FIGS. 2 and 3 depict an example system for estimating gantry orientation according to an embodiment.
Figure 3:
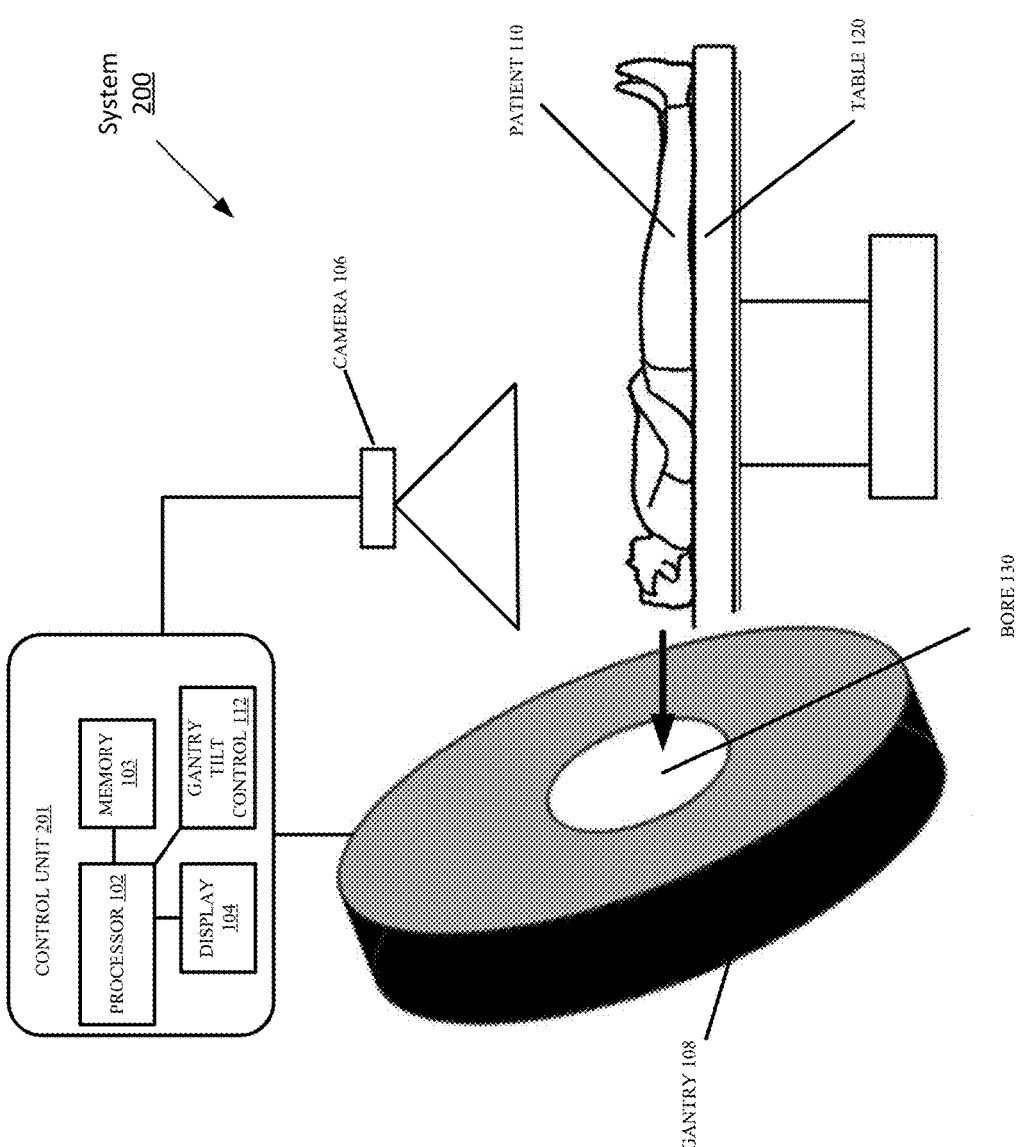

FIGS. 2 and 3 depict an example system 200 for estimating optimal gantry tilt and/or scanning parameters using image(s) from one or more cameras 106 for a CT scan of a patient 110. FIGS. 2 and 3 depict an un-tilted gantry 108 and a tilted gantry 108 respectively. The system 200 of FIGS. 2 and 3 includes a CT imaging system 100 including the gantry 108 and table 120, one or more cameras 106, and a control unit 201 including a processor 102, a memory 103, a display 104, and a gantry tilt control 112. The processor 102 may implement a machine-learned network stored in the memory 103. The control unit 201 may include or be components or modules in a computer, server, or cloud computing environment. Additional, different, or fewer components may be provided, such as not including the display 104 where the output is stored in a memory 103 or transferred over a network.

In an embodiment, the system 200 is configured to estimate optimal gantry tilt for head CT scans from patient camera images. In another embodiment, the system 200 estimates optimal scan range or other parameters for head CT scans from patient camera images. The one or more cameras 106 may include an in-bore camera 106 or an external ceiling mounted camera 106 for example. In an embodiment, the optimal gantry tilt and/or scan range are derived from internal landmarks detected using a machine learning system. Alternatively, the optimal gantry tilt and/or scan range are directly estimated using a machine learning system.

Advantages of this implementation include time and cost benefits, reliance on commonly used and available hardware (no specialized cameras or sensors), and ease of use. The systems and methods reduce the need for complex hardware (cost reduction) and improve speed (for example, by removing the need for a topogram). Training of technicians may be reduced as parameters are automatically determined and/or set. Patient safety may be improved along with improved diagnostics provided by the CT scan.

As described above in FIG. 1, the CT imaging system 100 is configured to acquire CT data of a patient 110 or an object which may be processed into an image or representation of the patient 110 or object. While the embodiments described herein are directed to CT scans, alternative imaging systems may be used that require patient positioning such as MRI or ultrasound. The CT imaging system 100 includes a gantry 108 that may be tilted using a gantry tilt control 112. The gantry 108 is a ring-shaped structure, containing the x-ray tube, collimators, filters, data acquisition system (DAS), associated electronics such as gantry angulation motors, rotational components including slip ring systems, and the detector array among other components. The gantry tilt control 112 may be included within or mounted on the gantry 108 and is configured to adjust the tilt of the gantry 108. To scan the patient 110, the patient table 120 is moved through the gantry aperture. The gantry tilt control 112 controls at least a gantry tilt angle. The gantry tilt angle is the angle between the vertical plane and the plane containing the x-ray beam and the detector array. The gantry angulation allows aligning the selected anatomic region with the scanning plane. The gantry 108 may, depending on the equipment and manufacturer, be angled up to 30 degrees forward or backward to accommodate a variety of patients and examination protocols.

The CT imaging system 100 is configured to perform a CT scan using a scanning protocol including one or more scan parameters. These scan parameters may include, for example, a detector configuration, a tube current, a tube potential, a reconstruction algorithm, patient positioning, a scan range, a reconstructed slice thickness, and a pitch among others. The adjustment of these parameters may be optimized to reduce patient radiation dose. In an example, tube-current modulation techniques may be used to adjust the tube current in the xy-plane (angular modulation), along the craniocaudal axis (z-axis modulation), or both, according to the attenuation of the patient 110 and x-ray beam direction. The scan range may be adjusted to limit the radiation dose applied to the eye lenses. The position of the patient 110 or the configuration of the CT scanner may be adjusted to also limit the radiation dose applied to the eye lenses. In an embodiment, the CT imaging system 100 does not include a gantry that is configured to tilt. In this case, the system 200 may provide scanning parameters or other positioning orientations such as the horizontal position of the patient/table in the gantry.

In an embodiment, the CT imaging system 100 includes one or more cameras 106 located in a bore 130 of the CT imaging system 100 or on the gantry 108. The one or more cameras 106 may also be located outside or separate from the CT imaging system 100, for example on the ceiling of the imaging room. The cameras 106 capture an image of the patient 110 or object as a two-dimensional distribution of pixels, such acquiring red, green, blue (RGB) values. Other information, such as depth information, may be captured as or as part of the image. Thermal, infrared, or another image may be captured.

In one embodiment, the camera 106 includes or is a depth sensor, such as a 2.5D or RGBD (RGB plus depth) sensor (e.g., a Microsoft Kinect 2 system or ASUS Xtion Pro). The depth sensor may directly measure depths, such as using time-of-flight, interferometry, or coded aperture. The depth sensor may be a camera 106 or cameras 106 capturing a grid projected onto the patient 110, and the processor 102 reconstructs an outer surface from the structured light in the image or images. The sensor may be or include multiple cameras 106 capturing 2D images from different directions, allowing reconstruction of the outer surface from multiple images without transmission of structured light. Other optical or non-ionizing sensors may be used, such as a LIDAR camera 106. In other embodiments, the camera 106 is an infrared camera or captures optical information at other wavelengths. The camera 106 may be a thermal camera. Infrared or another thermal camera may show temperature as part of the image. Alternatively, the camera 106 may be a typical camera 106 that just acquires image data.

The camera 106 or cameras 106 may be placed in various locations in the room, including attached or connected to the CT imaging system 100 itself. The camera(s) 106 may be positioned on a wall, ceiling, or elsewhere in the imaging suite or operating room, such as on a boom generally above the patient 110. For example, cameras 106 are fixed or attached to the ceiling of the scan room or operating room, on the scanner body, such as at the gantry 108 of the scanner, inside a bore 130 of the scanner, on an extended arm of the scanner, such as on Cone Beam CT scanner during radiation therapy, and/or on a radiation therapy scanner.

The camera 106 (camera sensor) is directed at a patient 110. The camera's field of view covers at least part of the patient's body during medical image acquisition or during radiation treatment. The camera 106 captures the outer surface of the patient 110 from one or more perspectives. In an embodiment, for a CT scan of a brain or head region, the camera 106 is configured to capture the head region of the patient 110 so that the anatomical head and neck structures of the patient 110 including but not limited to eyes, sinuses, inner ear, jaw, and the patient's skull may be estimated therefrom. Alternatively, depending on the type of scan and protocol other portions of the outer surface may be captured, such as the entire patient 110 viewed from one side from head to toe and hand to hand or just the head region. The camera 106 captures the outer surface with the patient 110 in a particular position, such as capturing a front facing surface as the patient 110 lies in a bed or on a table 120 for treatment or imaging. The outer surface is the skin of the patient 110. In other embodiments, the outer surface includes some clothing. The sensor may use a frequency that passes through clothing and detects skin surface. Alternatively, the outer surface includes clothing.

Figure 4:
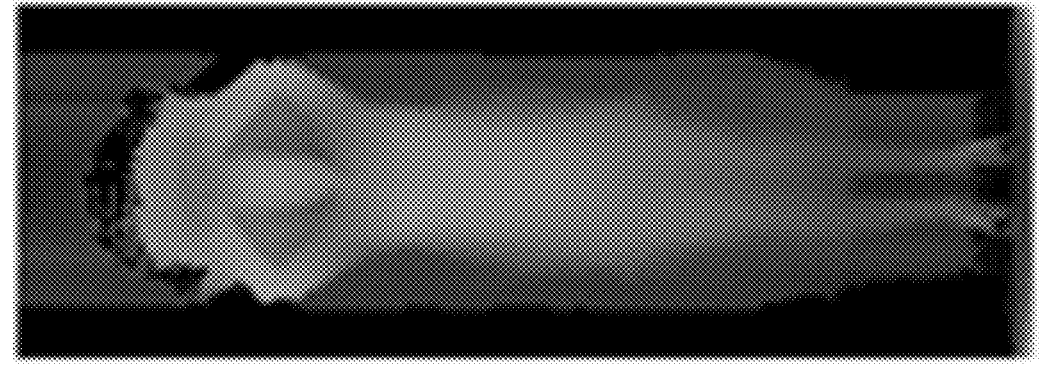
FIG. 4 depicts an example depth image of a patient according to an embodiment.
Figure 5:
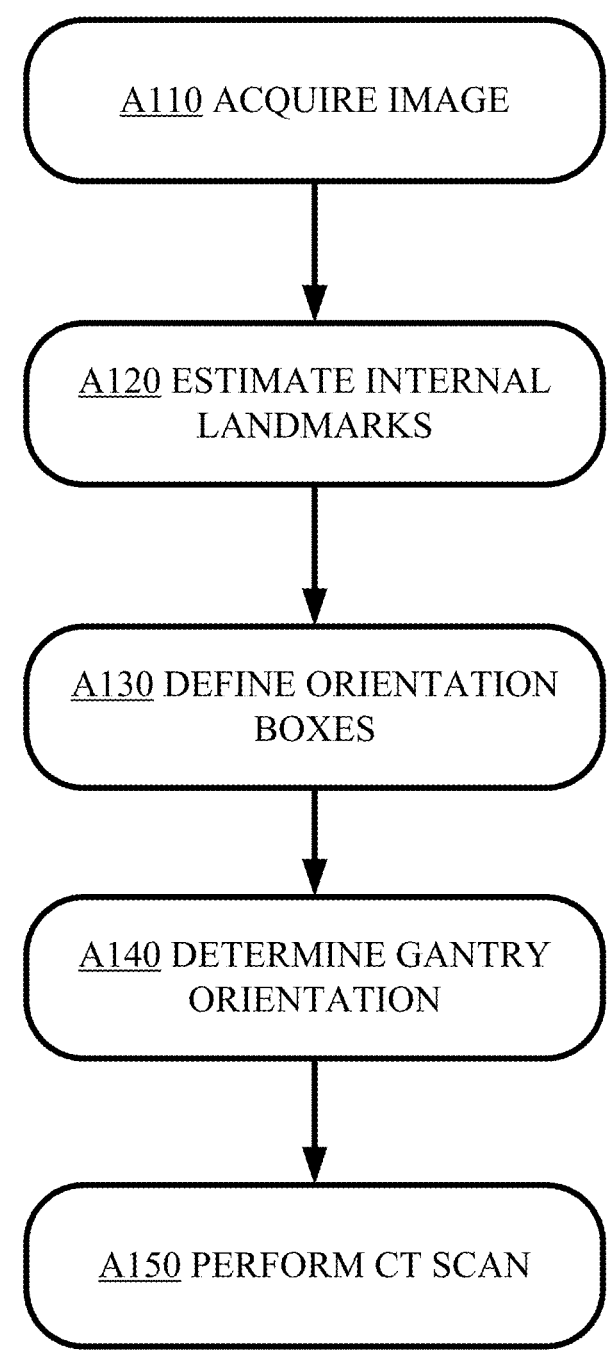
FIG. 5 depicts an example workflow for estimating gantry orientation according to an embodiment.

For depth data, the camera 106 may directly measure depth from the camera 106 to the user. The camera 106 may include a separate processor for determining depth measurements from images, or the processor 102 determines the depth measurements from images captured by the camera 106. A camera 106 may include a depth sensor such as LIDAR, 2.5D, RGBD, stereoscopic optical sensor, or other depth sensor. Infrared data may be acquired using an infrared sensor. An infrared sensor works the same way an object detection sensor does. The sensor may include an IR LED and an IR photodiode. Combining these two gives way to a photo-coupler or optocoupler. The IR LED is a transmitter emitting IR radiations. The radiation is detected by infrared receivers which are available in photodiodes form. The infrared photodiode responds to the infrared light generated by the infrared LED. The resistance of photodiode and the change in output voltage is directly proportional to the infrared light. After the infrared transmitter has produced an emission, it arrives at the object and some of the emission bounces or reflects back towards the infrared receiver. Based on the intensity of the response, the sensor output is decided by the IR receiver. In an embodiment, the depth and infrared data is derived from the image data. The camera 106 outputs the sensed pixels and/or depths. The measurements of the outer surface from the camera 106 are camera 106 or surface data for the patient 110. FIG. 4 depicts an example image from surface data where the intensity in grayscale is mapped to the sensed depth. Alternatively, the sensor measurements are processed to determine the outer surface information, such as stereoscopically determining the outer surface from camera images from different angles with image processing.

The surface data is used at the resolution of the sensor. For example, the surface data includes 256×256 pixels. Other sizes may be used, including rectangular fields of view. The surface data may be filtered and/or processed. For example, the surface data is altered to a given resolution. As another example, the surface data is down sampled, such as reducing 256×256 to 64×64 pixels. Each pixel may represent any area, such as each pixel as down sampled to 64×64 representing 1 cm2 or greater. Alternatively, the sensor captures at this lower resolution. The surface data may be cropped, such as limiting the field of view. Both cropping and down sampling may be used together, such as to create 64×64 channel data from 256×312 or other input channel data. In another approach, the surface data is normalized prior to input. The surface data is rescaled, resized, warped, or shifted (e.g., interpolation). The surface data may be filtered, such as low pass filtered.

More than one camera 106 may be used. For example, cameras 106 are positioned at different locations to capture camera data of the outer surface of the patient 110 from different perspectives. The images for any given time from the different cameras 106 may be used separately, such as where the different cameras 106 capture with different types of cameras 106 (e.g., RGBD and thermal cameras). In other embodiments, the camera data (images) from the different cameras 106 are combined, providing a scene. The input from one or more camera sensors may be processed to obtain a desired result stream. For example, point clouds from multiple RGBD cameras 106 are aligned based on known spatial relationship between the fixed cameras 106 and combined into a point cloud representing the patient 110 at that time. As another example, tomography or other three-dimensional (3D) processing is used to form a 3D scene from multiple two-dimensional (2D) images (e.g., RGB images from different perspectives used to determine depth of imaged points). In another example, multiple 2D images are stitched together to form another 2D image with a larger field of view. The resulting 2D image can be used in subsequent processing. In an embodiment, a first camera 106 located outside the gantry 108 is initially used to set the tilt angle of the gantry 108 while a second camera located inside the gantry 108 is used to adjust the tilt angle if the patient 110 moves.

The image or images are captured for a given time or continuously. Using continuous or defined frequency of capture, a stream of images from different times may be captured. The defined frequency may be preset, adjustable, or variable. In an embodiment, the images are captured continuously during the setup and scanning process. By capturing multiple images over time, the system may adjust the gantry tilt and/or scan parameters even if the patient 110 has moved or adjusted their position after being moved into the gantry 108. In alternative embodiments, an image or images for just one time are captured.

The processor 102 is configured to receive the images from the one or more cameras 106 and output an optimal gantry orientation and/or scan parameters. In certain embodiments, the processor 102 is configured to estimate internal landmarks from the one or more images in an intermediate step. The landmarks may be 3D or 2D. Alternatively, the processor 102 may directly estimate an optimal gantry tilt, optimal gantry horizontal/vertical position, table position, patient position, and/or scan parameters from the camera images. In other embodiments, the processor 102 is configured to generate orientation boxes from the estimated internal landmarks. The orientation boxes may be input into the CT imaging system 100 which determines the optimal gantry tilt and/or scan parameters. When using a topogram or scout scan, a control component of the CT imaging system 100 may take as input the scout scan (topogram) or scout scan derived landmarks and output the optimal gantry tilt and/or scan parameters. Since a scout scan is not used in the embodiments described herein, the processor 102 may estimate the landmarks or provide the orientation boxes in place of the topogram to the CT imaging system 100. In this way, the system may be applied to existing hardware or workflows that require such information from a topogram (while skipping the acquisition step). The processor 102 is a control processor, image processor, general processor, digital signal processor, three-dimensional data processor, graphics processing unit, application specific integrated circuit, field programmable gate array, artificial intelligence processor, digital circuit, analog circuit, combinations thereof, or other now known or later developed device. The processor 102 is a single device, a plurality of devices, or a network. For more than one device, parallel or sequential division of processing may be used. In one embodiment, the processor 102 is a control processor or other processor of a device. The processor 102 operates pursuant to and is configured by stored instructions, hardware, and/or firmware to perform various acts described herein.

The processor 102 may be configured to use a machine learned network or model for estimating internal landmarks, generating orientation boxes, and/or estimating the optimal gantry orientation and/or scan parameters. Different types of models or networks may be trained and used. In an embodiment, the machine learned network(s) or models may include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, one hundred nodes are provided. Later or subsequent units may have more, fewer, or the same number of nodes.

Different neural network configurations and workflows may be used for the network such as a convolution neural network (CNN), deep belief nets (DBN), or other deep networks. CNN learns feed-forward mapping functions while DBN learns a generative model of data. In addition, CNN uses shared weights for all local regions while DBN is a fully connected network (e.g., including different weights for all regions of a feature map. The training of CNN is entirely discriminative through backpropagation. DBN, on the other hand, employs the layer-wise unsupervised training (e.g., pre-training) followed by the discriminative refinement with backpropagation if necessary. In an embodiment, the arrangement of the trained network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

The training data for the model/network (and other networks) includes ground truth data or gold standard data. In an example, a scout scan may be used during a procedure in which one or more cameras 106 capture image(s) of a patient 110 for a CT imaging procedure. Internal landmarks are identified in the resulting image. The location of the internal landmarks and the images captured by the camera 106 make up the ground truth data that can be used to train a network to output locations of internal landmarks when provided with camera data. Different training data may be acquired and annotated for different tasks such as estimating internal landmarks, generating orientation boxes, and/or estimating the optimal gantry tilt, position, and/or scan parameters.

The machine learned network(s) and other data may be stored in a memory 103. The memory 103 may be or include an external storage device, RAM, ROM, database, and/or a local memory 103 (e.g., solid state drive or hard drive). The same or different non-transitory computer readable media may be used for the instructions and other data. The memory 103 may be implemented using a database management system (DBMS) and residing on a memory 103, such as a hard disk, RAM, or removable media. Alternatively, the memory 103 is internal to the processor 102 (e.g., cache). The instructions for implementing the processes, methods, and/or techniques discussed herein are provided on non-transitory computer-readable storage media or memories, such as a cache, buffer, RAM, removable media, hard drive, or other computer readable storage media (e.g., the memory 103). The instructions are executable by the processor 102 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor 102 or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The display 104 is configured to display or otherwise provide the model of the user to the user. The display 104 is a CRT, LCD, projector, plasma, printer, tablet, smart phone or other now known or later developed display device for displaying the output.

FIG. 4 depicts an example workflow for estimating an optimal gantry orientation for a CT scanning system. The method is performed by the system of FIG. 1, 2, 3, or another system. The method is performed in the order shown or other orders. Additional, different, or fewer acts may be provided. For example, scanning parameters may also be estimated based on the acquired images. As the patient 110 enters the gantry 108, images of the patient 110 are acquired, from which the method estimates internal landmarks of anatomical head and neck structures, including but not limited to eyes, sinuses, inner ear, jaw, and skull. The method defines protocol-dependent orientation boxes based on the internal landmarks that are then used to define the scan range and gantry orientation.

At act A110, at least one camera 106 acquires one or more images of a patient 110 prior to performing a medical imaging procedure, for example, as the patient 110 enters the gantry 108. The one or more images may include depth information, for example, as included in an RGBD image. The one or more images may be acquired while the patient 110 is positioned on a bed and/or while the patient 110 is moved in and out of the gantry 108. The gantry 108 of a computed tomography scanner is a ring or cylinder, into which a patient 110 is placed by either moving the bed on which the patient 110 is positioned or moving the gantry 108 (e.g., sliding gantry 108) while the patient 110 does not move. The gantry 108 is configured to tilt and/or move horizontally/vertically in order to avoid exposure to certain portions of a patient 110. The at least one camera 106 may be located on the gantry 108, inside or outside of the bore 130, on a ceiling apart from the CT scanner or any other location from which the at least one camera 106 may capture an image of the patient 110. Multiple cameras 106 may be used. Images may be captured at different times to make sure that any movement by the patient 110 is accounted for.

Figure 6:
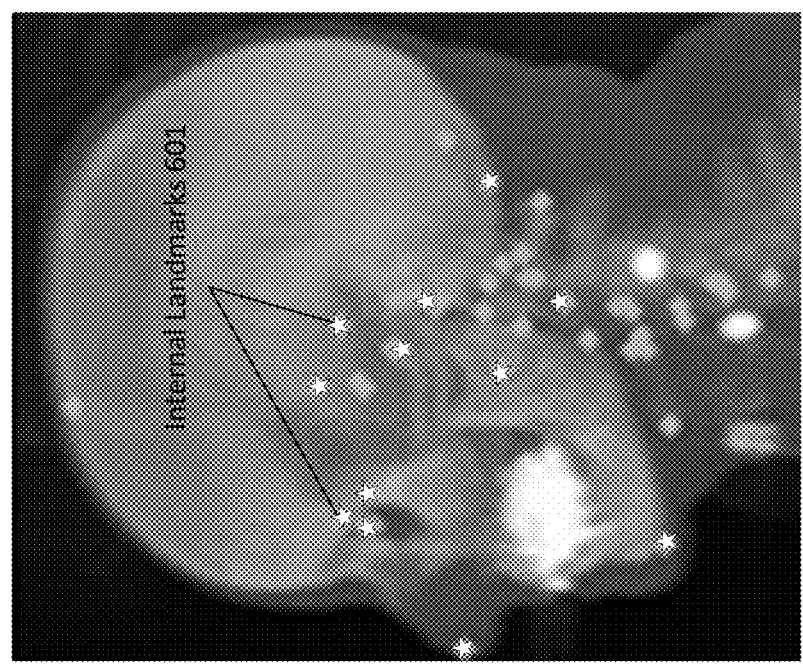
FIG. 6 depicts example internal landmarks according to an embodiment.

At act A120, a machine trained model estimates internal landmarks of the patient 110 from the one or more images. The internal landmarks may include, for example, the location(s) of the anatomical head and neck structures of the patient 110, including but not limited to eyes, sinuses, inner ear, jaw, and skull. Estimating the internal landmarks may include providing a 3D representation of the estimated anatomical head and neck structures of the patent with one or more labeled or identified landmarks. FIG. 6 depicts an example of the internal landmarks 601 of a patient 110 derived from one or more images of the patient 110. The landmarks 601 may be standard locations that describe anatomical features of a patient 110. In another embodiment, the representation is 2D or 3D.

In an embodiment, the internal landmarks are estimated directly from the one or more images. A machine trained model may be used that is configured to input the images and output one or more locations for specific landmarks, for example, the locations of the eyes, sinuses, inner ear, jaw, and skull. In an example, the machine trained network is configured as a classifier that segments or identifies landmarks/locations in the image data. In an example operation, the machine trained network is configured to segment an image (or volume) from the one or more cameras 106 and determine the internal landmarks therein. In order to configure the machine trained network, the network inputs the training data and outputs a segmented image or volume. The prediction is compared to, for example, a hand segmented image of the input data. A loss function may be used to identify the errors from the comparison. The loss function serves as a measurement of how far the current set of predictions are from the corresponding true values. Some examples of loss functions that may be used include Mean-Squared-Error, Root-Mean-Squared-Error, and Cross-entropy loss. Mean Squared Error loss, or MSE for short, is calculated as the average of the squared differences between the predicted and actual values. Root-Mean Squared Error is similarly calculated as the average of the root squared differences between the predicted and actual values. During training and over repeated iterations, the network attempts to minimize the loss function as the result of a lower error between the actual and the predicted values means the network has done a good job in learning. Different optimization algorithms may be used to minimize the loss function, such as, for example, gradient descent, Stochastic gradient descent, Batch gradient descent, Mini-Batch gradient descent, among others. The process of inputting, outputting, comparing, and adjusting is repeated for a predetermined number of iterations with the goal of minimizing the loss function.

The internal landmarks may be based on a surface model of the patient 110 generated from the one or more images, for example by segmenting the image data from the one or more cameras 106 and determining the locations of the internal landmarks from the segmented image. In an embodiment, a shape model is used and mapped to the surface model of the patient 110. The locations of landmarks in the shape model are mapped to the patient 110. In an example, the processor 102 fits a patient model to the surface data/segmented data from the image data. The patient model is a generic representation of surface of a human or part of a human. Different models may be used for different body types, such as a male or female model. The patient model is not specific to the patient 110. For example, the patient model is a statistical shape model. The patient model is not specific to any other patient or is specific to a patient meeting a norm. Any representation may be used for the model. In one embodiment, the model is formed from a mesh, such as a mesh of triangles. Other meshes may be used. Other representations of a three-dimensional surface may be used. Any now known or later developed fit of a body surface model to captured surface data for a patient 110 may be used. For example, a SCAPE model is fit to the surface data based on minimization of differences. In one embodiment, the depth camera image of a subject is converted to a three-dimensional point cloud. A plurality of anatomical landmarks is detected in the three-dimensional point cloud. A three-dimensional avatar mesh is initialized by aligning a template mesh to the three-dimensional point cloud based on the detected surface anatomical landmarks. A personalized three-dimensional avatar mesh of the subject is generated by optimizing the three-dimensional avatar mesh using a trained parametric deformable model (PDM). The optimization is subject to constraints that consider clothing worn by the subject and the presence of a table 120 on which the subject in lying. In an embodiment, a statistical shape model is fit to the depths as the surface data. The statistical shape model is a mesh or other representation of an average or other statistical representation of an outside of a human or part of a human. The statistical shape model includes probabilities or other constraints on alteration, so that the fitting maintains the shape based on statistics. In another embodiment, a personalized three-dimensional mesh of a person is generated by a model-based approach to fit a human skeleton model to depth image data of the person. The estimated pose skeleton is then used to initialize a detailed parametrized deformable mesh (PDM) that was trained in an offline training phase. The PDM is then optimized to fit the input depth data by perturbing the body pose and shape. A sampling-based optimization procedure fits the PDM to the depth data. Unlike the shape completion and animation of people (SCAPE) model, which is only applied to data with a skin clad subject, the sampling-based approach deals with clothing variations of the subject. Furthermore, the sampling-based approach also enables embodiments to deal with bias introduced due to sensor noise.

In an embodiment, the machine trained network is an image-to-image network, such as a generative adversarial network, trained to convert the acquired image data into a segmented image with identified internal landmarks. For example, the trained convolution units, weights, links, and/or other characteristics of the network are applied to the surface data and/or derived feature values to extract the corresponding features through a plurality of layers and output a segmented image with the internal landmarks. The features of the input images (e.g., surface data) are extracted from the images. Other more abstract features may be extracted from those extracted features using the architecture. Depending on the number and/or arrangement of units or layers, other features are extracted from the input. For training the machine trained network, the machine training network arrangement is defined. The definition is by configuration or programming of the training. The number of layers or units, type of training, and other characteristics of the network are controlled by the programmer or user. In other embodiments, one or more aspects (e.g., number of nodes, number of layers or units, or type of training) are defined and selected by the machine during the training. Any machine training architecture for outputting a spatial distribution from an input spatial distribution may be used. For example, U-Net is used. A convolutional-to-transposed-convolutional network is used. One segment of layers or units applies convolution to increase abstractness or compression. The most abstract feature values are then output to another segment. The other segment of layers or units then applies transposed convolution to decrease abstractness or compression, resulting in outputting of a segmented image including the internal landmarks.

Figures 7A, 7B:
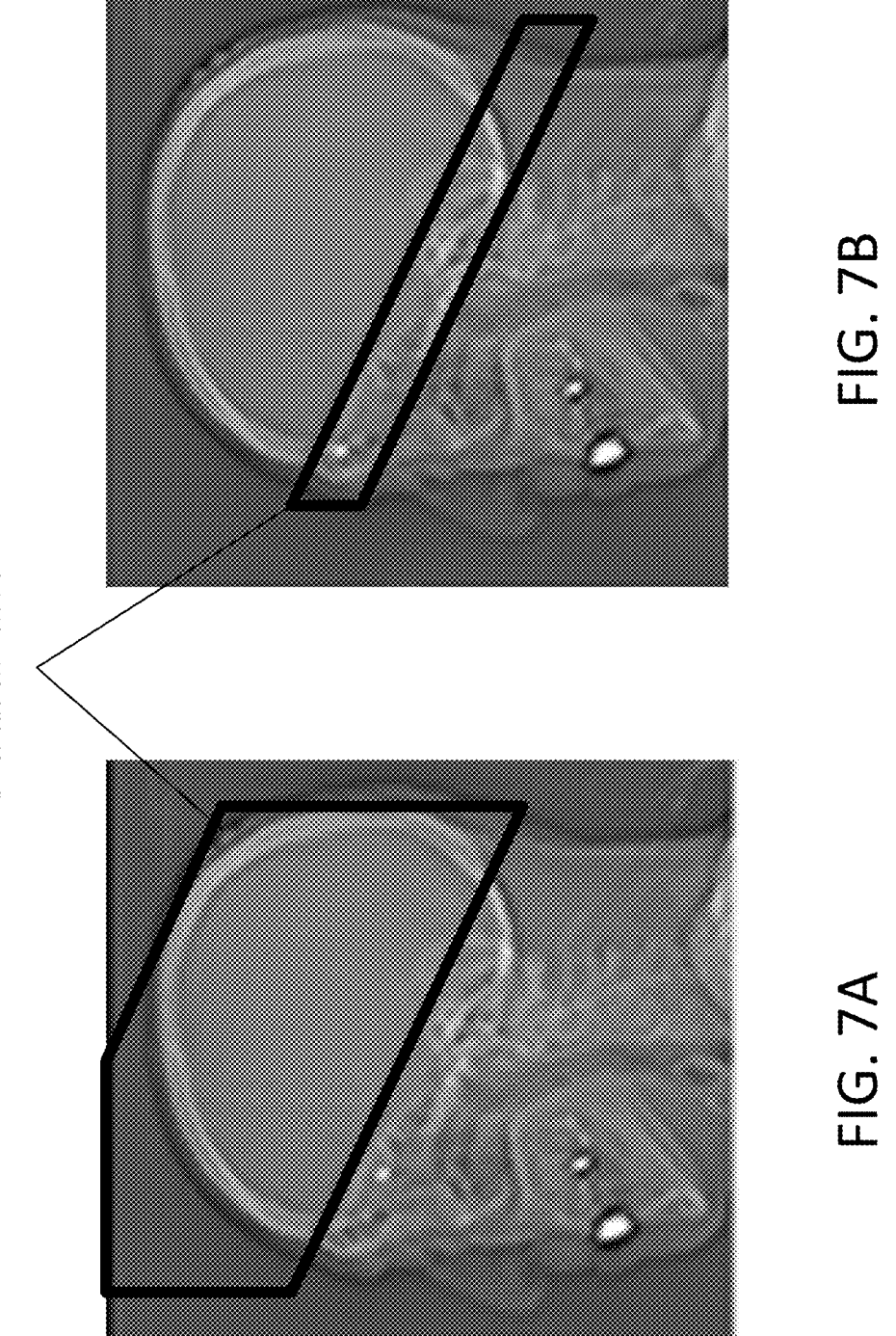
FIGS. 7A and 7B depict example orientation boxes according to an embodiment.

At act A130, the processor 102 defines protocol dependent orientation boxes based on the internal landmarks. The protocol dependent orientation boxes may represent the areas/regions that are to be scanned (or alternatively areas that are to be avoided), for example by representing slices that, if scanned, result in less radiation in certain areas such as the eye lenses. FIGS. 7A and 7B depicts an example of the orientation boxes 701. As depicted, the orientation boxes 701 describe the region of interest to be scanned and/or regions to be avoided. In an embodiment, orientation boxes are used as orientation boxes are required by the imaging or scanner software or protocol. The orientation boxes may be 2D or 3D.

At act A140, the processor 102 determines a gantry orientation based on the orientation boxes. The processor 102 may also determine scan parameters for the CT scan based on the orientation boxes, for example, an optimal scan range or tube current may be determined. The gantry orientation may include an angle of the gantry 108, horizontal position of the gantry 108, and/or vertical position of the gantry 108 that generates the slices or scan of an area defined by the orientation boxes. For example, the angle of the gantry 108 may be determined so that the slices described by the orientation boxes result from the scan. The gantry orientation may be provided by a gantry tilt operation. The gantry tilt operation may angle the gantry 108 by, for example, up to 30 degrees in either direction. The gantry tilt angle and operation may be dependent on the type of gantry 108/scanning system. The gantry orientation may also provide a horizontal location of the gantry 108 in relation to the table 120 or patient 110.

At act A150, a CT scan is performed where the gantry 108 is positioned using the gantry orientation. A gantry tilt control 112 angles the gantry 108 so that the optimal angle is set and the patient 110 is protected from excess radiation in certain areas that are sensitive to radiation. In an embodiment, the acts A110-A140 are preformed repeatedly while the patient 110 is on the table 120 or in the gantry 108. This allows the system to adjust the angle of the gantry 108 up until the moment the scan is performed in order to account for any patient 110 movement. In an example, a patient 110 may be placed on the table 120. An image taken from an overhead camera 106 is used by the system to generate an optimal gantry orientation. The gantry 108 is then tilted to provide this orientation. However, while the patient 110 is moved into the gantry 108 (or the gantry 108 is slid over the patient 110), the patient 110 may adjust a position of their head. A camera in the bore 130 of the gantry 108 acquires another image which leads to a different optimal gantry orientation based on the new position of the patient's head. A different angle is provided to the gantry tilt control 112, which adjusts the gantry 108 and the scan is performed.

The steps A120 and A130 may be performed due to existing systems requiring these intermediary steps. Certain existing systems may acquire a topogram or scout scan and identify internal landmarks/orientation boxes therefrom. Acquiring the topogram or scout scan takes time and may damage the patient 110. The method described above removes the need for the topogram/scout scan but maintains certain aspects such as the internal landmarks and orientation boxes so that it may be implemented using existing systems. In an alternative embodiment, the optimal gantry tilt and/or scanning parameters may be generated directly from the image data.

Figure 8:
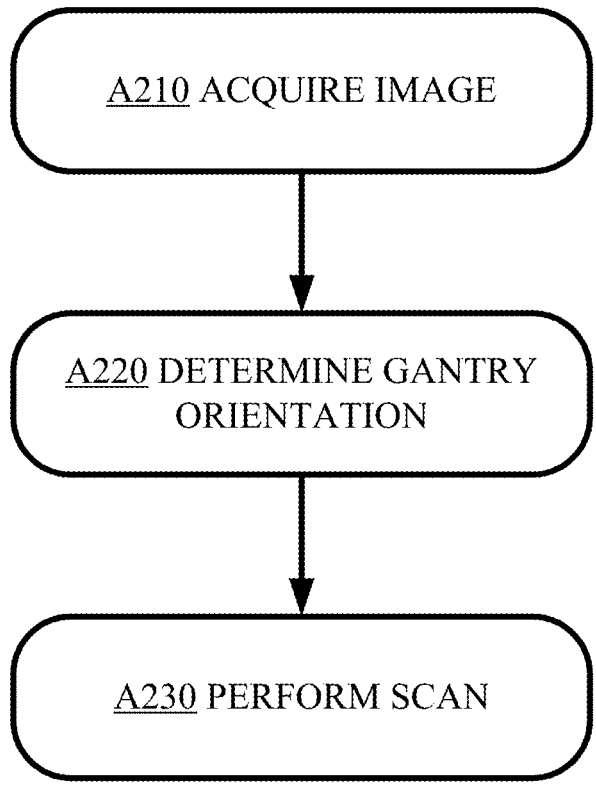
FIG. 8 depicts an example workflow for estimating gantry orientation according to an embodiment.

FIG. 8 depicts a workflow for directly determining a gantry tilt or scanning parameters from images. The method is performed by the system of FIG. 1, 2, or another system. As the patient 110 enters the gantry 108, images of the patient 110 are acquired, from which the method estimates the scan range and/or gantry orientation. The method is performed in the order shown or other orders. Additional, different, or fewer acts may be provided.

At act A210, at least one camera 106 acquires one or more images of a patient 110. The camera 106 captures surface data representing an outer surface of a patient 110, for example, the head region of the patient 110. The camera 106 is directed at the patient 110. The camera 106 may capture two-dimensional data or three-dimensional data. The camera 106 may capture depth information. The camera 106 captures the outer surface of the patient 110 from one or more perspectives. Any portion of the outer surface may be captured, such as the entire patient 110 viewed from one side from head to toe and hand to hand or just the head region. The camera 106 captures the outer surface with the patient 110 in a particular position, such as capturing a front facing surface as the patient 110 lies in a bed or on a table 120 for treatment or imaging. Multiple cameras 106 may be used to capture image data of the patient 110, for example, a camera 106 located on a ceiling above the patient 110 and a camera 106 located in the bore 130 of the gantry 108.

In an embodiment, the patient data may be segmented and/or fit to a patient model. The image data acquired by the camera 106 may represent the surface data of the patient 110. In an embodiment, a patient model may be fit to the surface data. The patient model is a generic representation of surface of a human or part of a human. Different models may be used for different body types, such as a male or female model. The patient model is not specific to the patient 110. For example, the patient model is a statistical shape model. The patient model is not specific to any other patient 110 or is specific to a patient meeting a norm. Any representation may be used for the model. In one embodiment, the model is formed from a mesh, such as a mesh of triangles. Other meshes may be used. Other representations of a three-dimensional surface may be used.

At act A220, a machine trained model determines a gantry orientation from the one or more images or the fit patient model. The machine trained model inputs the image data and outputs an optimal gantry tilt and/or scanning parameters such as a scan range or tube current. The machine trained model is configured or trained by repeatedly inputting training data such as image data into the model and comparing the output of the optimal gantry tilt or scanning parameters to the expected (annotated) outcome. The annotated outcome may be based on previous procedures that included image data of the patient 110 from the one or more cameras 106 and a manually set or automatically set gantry tilt or scanning parameters based on, for example, a topogram. An example of a set of training data may include a patient image and the resulting optimal gantry tilt/scanning parameters. The resulting optimal gantry tilt/scanning parameters may be generated using a topogram or manually set by a technician. In a simple case, the model takes input variables (x) and an output variable (Y). The model learns the mapping function from the input to the output. $Y=f(X)$. The goal is to approximate the mapping function so well that when input new input data (x) the model can predict the output variables (Y) for that data.

In an embodiment, the network is a convolutional neural network (CNN), however other networks may be used. CNN learns feed-forward mapping functions. In addition, CNN uses shared weights for all local regions. The training of CNN is entirely discriminative through backpropagation. The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

At act A230, a CT scan is performed, wherein the gantry 108 is positioned using the gantry orientation. The gantry 108 is positioned at an angle that provides the optimal gantry orientation as output by the machine trained model. The gantry orientation may also provide a horizontal/vertical location for the gantry 108. The steps A210 and 220 may be performed continuously or at regular intervals in order to account for movement of the patient 110 after an initial image is acquired. After the gantry 108 is tilted to the correct angle, the scan is initialized by the CT scanner with the scan parameters provided by the machine trained model or as indicated by a scanning protocol.

In an embodiment, the imaging system is a CT scanner as described above. In alternative embodiments, the imaging system includes a MR, PET, SPECT system, or a therapeutic radiation scanner, such as an x-ray or particle therapy system. The imaging scanner operates pursuant to the determined scanning parameters to treat or image a patient 110. The settings and scanning parameters control the location in the patient 110 being scanned, the type of scan (e.g., pulse sequence), and/or radiation dose. The intensity, frequency, duration, and/or other settings are controlled, at least in part, based on the output of the machine trained model. In one embodiment, the imaging system uses the optimal gantry orientation to control a position and/or movement of a bed upon which the patient is placed. Once configured by the settings, the imaging system treats or images the patient 110. For therapy, the amount of radiation applied is based, at least in part, on the acquired images as the scanning parameters of the scanner are determined based on the output of the machine trained model and not from a scout scan. For imaging, the imaging system is configured to scan an internal region of a patient 110 and generate diagnostic information from the scan.

It is to be understood that the elements and features recited in the appended claims may be combined in different ways to produce new claims that likewise fall within the scope of the present invention. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

What is claimed is:

1. A method for estimating an optimal gantry orientation for a CT scan using a CT scanning protocol without using a scout scan, the method comprising:

acquiring, by at least one camera, one or more images of a patient;

estimating, using an image to image network, 3D internal landmarks of the patient from the one or more images, wherein the image to image network is trained to convert the one or more images into a segmented image with identified internal landmarks;

defining, based on the estimated 3D internal landmarks and the CT scanning protocol, one or more protocol dependent 3D orientation boxes, each orientation box comprising a geometric volume defined in a coordinate system of the CT scanner and representing at least one of a scan region or an avoidance region for the CT scanning protocol;

determining the optimal gantry orientation by evaluating an orientation of a CT scan plane relative to the one or more protocol dependent 3D orientation boxes to satisfy protocol-specific scan constraints without acquisition of a scout scan; and performing the CT scan with the CT scanning protocol, by the CT scanner, wherein a gantry of the CT scanner is positioned using the optimal gantry orientation.

2. The method of claim 1, further comprising:

determining an optimal scan range based on the protocol dependent 3D orientation boxes, wherein the CT scan is performed using the optimal scan range.

3. The method of claim 1, wherein the at least one camera comprises an RGBD camera.

4. The method of claim 1, wherein the at least one camera is located inside a bore of the gantry.

5. The method of claim 1, wherein the optimal gantry orientation comprises tilting the gantry in order to keep the patient's eye lenses outside a range of a beam during the CT scan.

6. The method of claim 1, wherein the optimal gantry orientation comprises moving the gantry horizontally in order to keep the patient's eye lenses outside a range of a beam during the CT scan.

7. The method of claim 1, wherein the steps of acquiring, estimating, defining, and determining are repeated continuously while the patient is in the gantry.

8. A method for estimating gantry orientation of a gantry for a CT scan without using a scout scan, the method comprising:

acquiring, by at least one camera, one or more images of a patient;

defining a CT scanning protocol for the CT scan by a CT scanner;

defining using a machine learning system, the one or more images, and the CT scanning protocol, one or more protocol dependent 3D orientation boxes, each protocol dependent 3D orientation box comprising a geometric volume defined in a coordinate system of the CT scanner and representing at least one of a scan region or an avoidance region for the CT scanning protocol;

determining an optimal gantry orientation directly from the one or more protocol dependent 3D orientation boxes; and performing the CT scan, wherein the gantry is positioned using the optimal gantry orientation.

9. The method of claim 8, wherein the at least one camera comprises an RGBD camera.

10. The method of claim 8, wherein the at least one camera is located inside a bore of the gantry.

11. The method of claim 8, wherein the gantry orientation comprises tilting or adjusting a position of the gantry in order to keep the patient's eye lenses outside a range of a beam during the CT scan.

12. The method of claim 8, wherein the steps of acquiring and determining are repeated continuously while the patient is in the gantry.

13. The method of claim 8, further comprising:

determining, using the machine learning system, one or more scanning parameters from the one or more images; wherein the CT scan is performed with the one or more scanning parameters.

14. The method of claim 8, wherein the one or more images cover at least a head region of the patient.

15. A system for estimating gantry orientation for CT scans without using a topogram, the system comprising:

at least one camera configured to acquire one or more images of a patient;

a CT scanning system configured to perform a scan of the patient, the CT scanning system comprising at least a gantry and a gantry control system; and a control unit configured to determine an optimal gantry orientation based on the one or more images using at least an image to image network trained to convert the one or more images into a segmented image with identified three-dimensional internal landmarks that are used to define one or more protocol dependent 3D orientation boxes, each orientation box comprising a geometric volume defined in a coordinate system of the CT scanner and representing at least one of a scan region or an avoidance region for the CT scanning protocol, determine an optimal gantry orientation by evaluating an orientation of a CT scan plane relative to the one or more protocol dependent 3D orientation boxes to satisfy protocol-specific scan constraints without acquisition of a scout scan, and adjust the gantry using the gantry control system.

16. The system of claim 15, wherein the at least one camera comprises an RGBD camera.

17. The system of claim 15, wherein the at least one camera is located inside a bore of the gantry.

18. The system of claim 15, wherein the optimal gantry orientation comprises tilting or adjusting a position of the gantry in order to keep the patient's eye lenses outside a range of a beam during the scan.

* * * * *